United States Patent [19]
Davenport et al.

[11] Patent Number: 5,989,194
[45] Date of Patent: Nov. 23, 1999

[54] METHOD AND APPARATUS FOR DETECTING OCULAR DISEASE AND ABNORMALITIES

[75] Inventors: Wayne E. Davenport, Huntsville, Ala.; Jack R. Bellows, Memphis, Tenn.

[73] Assignees: Vision Partners, L.P., Memphis, Tenn.; The United States of America, as represented by the Secretary of the Army, Washington, D.C.

[21] Appl. No.: 09/020,977

[22] Filed: Feb. 9, 1998

[51] Int. Cl.$^6$ ................................................. A61B 13/00
[52] U.S. Cl. ............................................................. 600/558
[58] Field of Search ............................ 600/558; 351/211, 351/221

[56] References Cited

U.S. PATENT DOCUMENTS

| | | | |
|---|---|---|---|
| 3,891,311 | 6/1975 | Fletcher et al. | 351/38 |
| 4,648,052 | 3/1987 | Friedman et al. | 364/550 |
| 5,204,703 | 4/1993 | Hutchinson et al. | 351/210 |
| 5,262,806 | 11/1993 | Szirth | 351/210 |
| 5,307,097 | 4/1994 | Baker | 351/212 |
| 5,355,895 | 10/1994 | Hay | 128/745 |
| 5,374,967 | 12/1994 | Hideshima et al. | 351/208 |
| 5,543,866 | 8/1996 | Van de Velde | 351/221 |
| 5,632,282 | 5/1997 | Hay et al. | 128/745 |
| 5,668,621 | 9/1997 | Nanjo | 351/206 |

*Primary Examiner*—Max Hindenburg
*Attorney, Agent, or Firm*—Garvey, Smith, Nehrbass & Doody, LLC

[57] ABSTRACT

A detection device for detecting ocular disease and abnormalities in human eyes. The ocular disease and abnormality detection device includes a photo-imaging device having a lens aligned on a selected optical axis. A flash unit generates a flash beam of light generally along the optical axis to produce retinal reflections from a patient's eyes. The retinal reflections from the patient's eyes are recorded by the photo-imaging device and displayed on a video display screen. A beamsplitter is positioned on the optical axis to pass the flash beam of light from the flash device to the patient's eyes, and to pass the retinal reflection from the patient's eyes to the photo-imaging device. A visual image is projected on a surface of the beamsplitter which appears to the patient's eyes as being positioned on the optical axis and generally superimposed on the lens of the photo-imaging device. The patient's eyes generally focus on the lens of the photo-imaging device as the patient views the projected image. A separate camera and video display is provided to monitor the patient's face. Patient information is preferably recorded with the retinal reflections from the patient's eyes. Methods of detecting ocular disease and abnormalities are also disclosed.

26 Claims, 3 Drawing Sheets

METHOD AND APPARATUS FOR DETECTING OCULAR DISEASE AND ABNORMALITIES

The invention described herein may be manufactured, used, and licensed by or for the Government for governmental purposes without the payment of any royalties thereon.

FIELD OF THE INVENTION

The present invention relates generally to testing apparatus for testing eyes of a patient and, more particularly, to a detection device for identifying ocular disease and abnormalities in human eyes.

BACKGROUND OF THE INVENTION

Detection of ocular disease and abnormalities in preschool children is important to prevent long-term vision impairment. During early development, the child's brain attempts to process visual information that is received in both of the child's eyes. However, if an ocular malady or impairment exists in one of the child's eyes which goes untreated for an extended period of time, the brain eventually stops processing information from the diseased eye, and leads to the severe ocular condition of amblyopia. Treatment of amblyopia is required at an early stage of child development before the condition becomes irreversible.

While early detection of ocular disease and abnormalities in preschool children is desirable, the ability of an ophthalmologist to identify certain eye maladies in young children is complicated by the age of the child, and in many cases, the inability of the child to communicate with the ophthalmologist. Common diseases and abnormalities which must be detected and treated in children include misalignment of the optical axes of the eyes (strabismus), refractive errors which cause nearsightedness (myopia) and farsightedness (hypermetropia), astigmatism, scarring of the cornea, and cataracts.

In the past, ocular screening of a patient's eyes has been achieved by flashing a beam of light at the patient's eyes, and recording retinal reflections from the patient's eyes on conventional 35 mm film or a charged coupled device (CCD). In this known procedure, the flash beam of light is positioned to travel off of, but nearly coincident with, an optical axis defined by the patient's eyes. The incoming flash beam of light is refracted by the lens of the patient's eye and falls generally on the pigmented macula and fovea of the patient's eye. A portion of the incoming light is reflected from the retina as a retinal reflection or retinal reflex which is then recorded by the camera for later evaluation by an ophthalmologist. Based on an evaluation of the retinal reflection, which may take days or even months to develop and review, the ophthalmologist is able to identify and correct certain ocular maladies.

In this ocular screening process, it is critical that the patient's eyes focus on the camera lens, and that the camera lens focus on the patient's eyes. Thus, alignment of the child's eye on the optical axis of the camera lens must be maintained throughout the screening procedure to insure that accurate retinal reflections are recorded. To focus the child's eye on the lens of the camera, known systems have used a series of lights, images, or an audible sound source positioned at or near the camera lens to attract the child's eyes to the camera lens. Other ocular systems have included a defocusing mechanism that presents an image having two focal lengths to defocus the eyes of the patient during the screening procedure.

Notwithstanding the advancements made in the prior art in the field of ocular screening devices for children, there is a need for an ocular disease and abnormality detection device which improves focusing of a patient's eyes on the lens of a camera during the screening procedure. There is also a need for an ocular disease and abnormality detection device which improves alignment verification of the patient's eyes before a retinal reflection is recorded. There is also a need for an ocular disease and abnormality detection device that rapidly processes and displays the recorded retinal reflections to provide faster evaluation of the information contained in the retinal reflection.

SUMMARY OF THE INVENTION

To these ends, the present invention sets forth an ocular disease and abnormality detection device that includes a headrest for supporting the head of a patient and aligning the patient's eyes on a selected optical axis. A photo-imaging device having a lens operable to receive a retinal reflection from the patient's eyes is aligned on the optical axis and spaced from the headrest a predetermined focal distance. A flash unit generates a flash beam of light generally along the optical axis and produces retinal reflections from the patient's eyes which are recorded by the photo-imaging device.

A beamsplitter is positioned on the optical axis intermediate the photo-imaging device and the headrest. The beamsplitter is operable to pass the flash beam of light from the flash unit to the patient's eyes, and to pass the retinal reflections from the patient's eyes to the lens of the photo-imaging device.

A visual stimulus generator projects a visual image on a surface of the beamsplitter which appears to the patient's eyes as being aligned on the optical axis and generally superimposed on the lens of the photo-imaging device at the predetermined focal distance. Advantageously, the patient's eyes generally focus on the lens of the photo-imaging device while the patient views the projected visual image to permit accurate retinal reflections from the patient's eyes to be recorded by the photo-imaging device. The video stimulus generator is preferably operable to vary the brightness of the projected image to allow pupil dilation adjustment in the patient's eyes.

In one aspect of the invention, the photo-imaging device comprises a digital camera for electronically recording retinal reflections from the patient's eyes. A data processing unit is coupled to the digital camera for receiving and storing the electronically recorded retinal reflections. A color video display screen is coupled to the data processing unit for displaying the recorded retinal reflections of the patient's eyes.

Preferably, the visual display generator comprises a video cassette player which generates moving visual images. A color video display screen is coupled to the video cassette player for projecting the moving visual image on the surface of the beamsplitter. The moving visual image attracts the attention of the patient and assists in focusing the eyes of the patient on the lens of the digital camera.

A greyscale camera is preferably focused on the face of the patient to provide a real-time image of the patient's face. The patient's face is illuminated by an infrared light source, such as a series of infrared light emitting diodes, which emit infrared light invisible to the patient's eyes. A greyscale video display screen is coupled to the video camera for displaying the real-time image of the patient's face. The greyscale video camera and video display screen allow the ophthalmologist or photoscreening technician to readily check the patient's eyes for proper alignment and pupil dilation before a retinal reflection is recorded.

A data entry device, such as a keyboard, is coupled to the data processing unit for entering selected patient information which is stored and displayed with the recorded retinal reflection from the patient's eyes. Alternatively, a flat video display screen is positioned adjacent the headrest for displaying selected patient information. The patient information displayed on the video display screen is recorded by the photo-imaging device with retinal reflections from the patient's eyes.

In accordance with a preferred method of the present invention, the eyes of a patient are aligned on a selected optical axis. A lens of a photo-imaging device is aligned on the optical axis and spaced from the patient's eyes a predetermined focal distance. A flash beam of light is directed generally along the optical axis to produce retinal reflections from the patient's eyes. A beamsplitter is provided on the optical axis to pass the flash beam of light to the patient's eyes, and to pass the retinal reflections from the patient's eyes to the lens of the photo-imaging device. A visual image is projected on the beamsplitter which appears to the patient's eyes as being aligned on the optical axis and generally superimposed on the lens of the photo-imaging device at the predetermined focal distance. The patient's eyes generally focus on the lens of the photo-imaging device while the patient views the projected image. Retinal reflections from the patient's eyes are recorded with the photo-imaging device.

The above features and advantages of the present invention will be better understood with reference to the accompanying figures and detailed description.

BRIEF DESCRIPTION OF THE DRAWINGS

Reference will now be made to the accompanying figures from which the novel features and advantages of the present invention will be apparent.

DETAILED DESCRIPTION OF THE INVENTION

Figure 1:
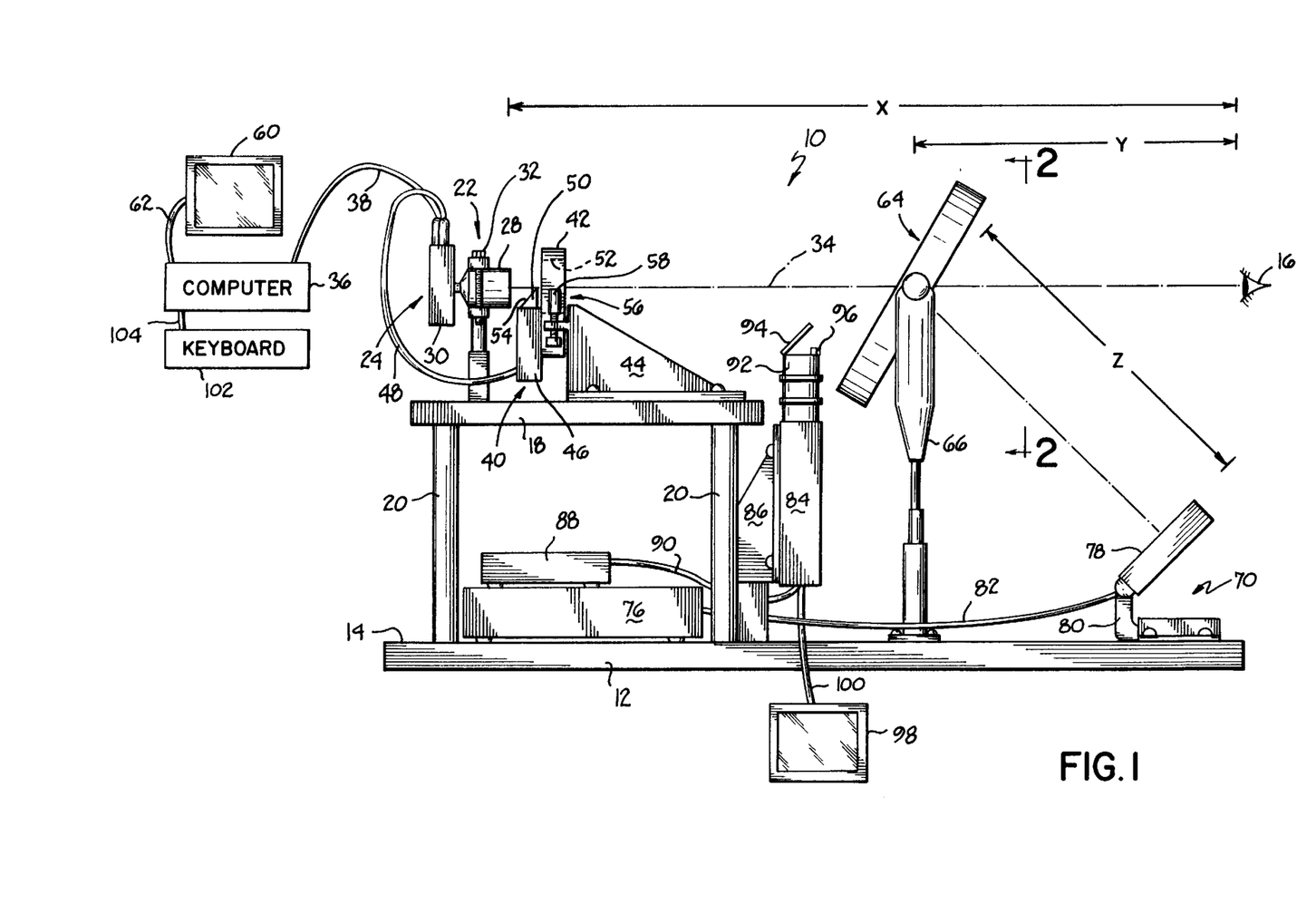
FIG. 1 is a side elevational view of an ocular disease and abnormality detection device in accordance with the principles of the present invention.

With reference to the figures, and to FIG. 1 in particular, an ocular disease and abnormality detection device 10 is shown in accordance with the principles of the present invention. Ocular disease and abnormality detection device 10 is particularly adapted for use by ophthalmologists or photoscreening technicians to identify various diseases or abnormalities which can occur in a patient's eyes. The various eye diseases and abnormalities which may be detected by the present invention include, by way of example, misalignment of the optical axes of the eyes (strabismus), refractive errors which cause nearsightedness (myopia) and farsightedness (hypermetropia), astigmatism, scarring of the cornea, and cataracts. As will be described in more detail below, ocular disease and abnormality detection device 10 is adapted to generate a flash beam of light toward a patient's eyes, and to record and display a retinal reflection of the patient's eyes for immediate or future evaluation by the ophthalmologist. Based on the visual characteristics of the retinal reflection, various diseases and abnormalities in the patient's eyes may be readily identified.

As shown most clearly in FIG. 1, ocular disease and abnormality detection device 10 includes, in one embodiment, a rigid horizontal platform 12 which is adapted to provide a level support surface 14 above a floor (not shown) for mounting various components of the detection device 10. At one end of detection device 10, remote from a patient's eyes 16 (one shown), a raised horizontal platform 18 is mounted on vertical support members 20 which extend upwardly from the support surface 14. A clamp assembly 22 is mounted to the raised platform 18 for supporting a photo-imaging device 24 which is used to record retinal reflections 26 (FIGS. 3–6) of the patient's eyes 16 during the ocular disease and abnormality detection procedure as will be described in detail below.

Photo-imaging device 24 preferably includes an optical lens 28 which is attached to a body 30 of the photo-imaging device 24 by conventional C-mount. Clamp assembly 22 includes a holding bracket 32 adapted to securely hold the optical lens 28 in alignment with an optical axis 34 which is coincident with the position of the patient's eyes 16. Lens 28 of photo-imaging device 24 is spaced from the patient's eyes 16 a predetermined focal distance "X", and preferably faces the patient's eyes 16 for receiving the retinal reflections. Operation of photo-imaging device 24 is preferably controlled by a computer 36 which is coupled to the photo-imaging device 24 through a cable 38. The computer sends command signals to the photo-imaging device 24, and the photo-imaging device 24 sends recorded retinal reflections 26 from the patient's eyes 16 to the computer 36.

In accordance with the present invention, the photo-imaging device 10 preferably comprises a color digital camera which is adapted to electronically record the retinal reflections 26 (FIGS. 3–6) from the patient's eyes 16. A 30-bit color digital camera suitable for this purpose is commercially available from Sound Vision of Framingham, Mass., and designated the "OEM Camera". The lens 28 of photo-imaging device 24 is preferably a 55 mm video-type lens with an F-stop of 4. While a color digital camera is preferred, it is contemplated that other photo-imaging devices, such as a standard 35 mm greyscale camera or other charge coupled device (CCD) cameras are possible without departing from the spirit and scope of the present invention.

As shown most clearly in FIG. 1, a flash unit 40 and ring body 42 are also supported on raised platform 18 through a bracket 44. Flash unit 40 includes a vertically adjustable flash device 46 which is coupled to photo-imaging device 24 through cable 48 for receiving a flash command from the photo-imaging device 24. Flash device 46 is preferably mounted off the optical axis 34 for generating a flash beam of light upwardly on a vertical axis transverse to the optical axis 34. A right-angle prism 50 is supported on the flash device 46 for directing the flash beam of light through an aperture 52 in ring body 42 and toward the patient's eyes 16. Prism 50 turns the flash beam of light from the upward direction on the vertical axis to align generally with the optical axis 34. Surface 54 of prism 50 is preferably painted with an opaque material to prevent transmission of light from flash device 46 to the lens 28 of photo-imaging device 24.

Vertical adjustment of flash device 46 and its associated right-angle prism 50 relative to the optical axis 34 is provided by a spring-loaded micrometer mount 56. By incrementally rotating a micrometer screw 58 in opposite directions, the angular separation between the flash beam of light and the optical axis 34 may be adjusted in a range from about 1° to about 5° to respectively increase or decrease the sensitivity of the ocular disease and abnormality detection device 10 as will appreciated by those skilled in the art. In accordance with the principles of the present invention, the flash beam of light generated by flash device 46 produces retinal reflections 26 from the patient's eyes 16 (FIGS. 3–6) which are recorded by photo-imaging device 24 and preferably received and stored in computer 36. A color video display screen 60 is preferably coupled to computer 36 through cable 62 for displaying selected color retinal reflections 26 from a patient's eyes 16.

Figure 2:
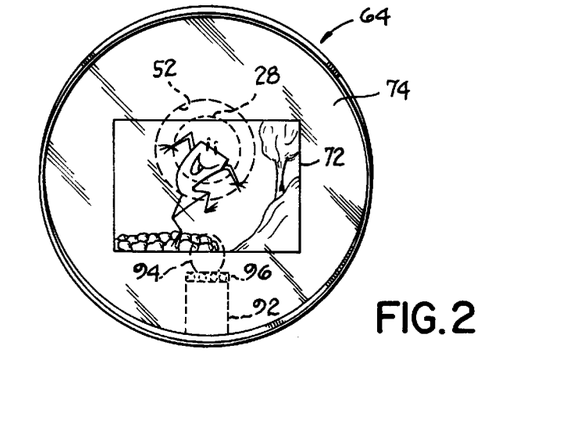
FIG. 2 is a schematic view showing a patient's view of the ocular disease and abnormality detection device of the present invention, taken along line 2—2 of FIG. 1.

As shown most clearly in FIGS. 1 and 2, a substantially transparent pellicle beamsplitter 64 is pivotally supported on an adjustable stand 66 mounted to the support surface 14 and spaced a predetermined focal distance "Y" from the patient's eyes 16. Beamsplitter 64 is preferably positioned on optical axis 34 intermediate the photo-imaging device 24 and an adjustable headrest 68 (FIG. 7) which is provided to support the patient's head in a fixed position and align the patient's eyes 16 on the optical axis 34. Adjustable headrest 68 does not form part of the present invention per se, and may comprise an adjustable chin rest or any other device suitable for supporting a patient's head and aligning the patient's eyes on the optical axis 34. Beamsplitter 64 is made of a thin membrane, such as MYLAR or similar material, and is preferably about 92% light transmissive and about 8% reflective. In accordance with the present invention, beamsplitter 64 is operable to pass the flash beam of light from flash device 46 to the patient's eyes 16, and to pass the retinal reflections 26 from the patient's eyes 16 to the lens 28 of photo-imaging device 24. To accommodate for light transmission loss through the beamsplitter 64, the brightness of the flash beam of light generated by flash device 46 is preferably adjustable to an acceptable brightness level.

As shown most clearly in FIGS. 1 and 2, a visual stimulus generator 70 is provided to assist in focusing the patient's eyes 16 on the lens 28 of photo-imaging device 24 during the ocular disease detection procedure of the present invention. Visual stimulus generator 70 is spaced a predetermined focal distance "Z" from beamsplitter 64, and is operable to project a visual image 72 (FIG. 2) on a surface 74 of the beamsplitter 64 which faces the patient's eyes 16. The sum of the focal distances "Y" and "Z" preferably equals the focal distance "X" such that the projected image 72 appears to the patient's eyes 16 as being aligned on the optical axis 34 and generally superimposed on the lens 28 of photo-imaging device 24. By superimposing the projected image 72 on the lens 28 of photo-imaging device 24 during the ocular disease and abnormality detection procedure of the present invention, the patient's eyes 16 generally focus on lens 28 to permit accurate retinal reflections 26 of the patient's eyes 16 to be recorded by the photo-imaging device 24.

Still referring to FIGS. 1 and 2, visual stimulus generator 70 preferably includes a video cassette player (VCP) 76 which is adapted to generate moving visual images 72 (FIG. 2) from a standard VHS tape (not shown). A flat video display screen 78 is pivotally supported on a stand 80 mounted to the support surface 14. Video display screen 78 is coupled to the video cassette player through cable 82 for projecting the moving visual images 72 on the surface 74 of beamsplitter 64. The moving visual images 72, such as animated cartoons, are preferably selected to draw and keep the attention of a preschool patient during the ocular disease detection procedure of the present invention. It will be appreciated that other devices for projecting a visual image on surface 74 of the beamsplitter 64 are possible without departing from the spirit and scope of the present invention. For example, visual stimulus generator 70 could include a video laser disc player, a digital video disc player, a computer for generating images in retrograde fashion, or a standard image projector as will be appreciated by those skilled in the art. Preferably, one or more speakers (not shown) are connected to the video cassette player 76 and positioned near photo-imaging device 24 to further attract the child's eyes to the camera lens 28.

Referring to the embodiment of FIG. 1, the ocular disease and abnormality detection device 10 includes a greyscale video camera 84 which is mounted to the support surface 14 through a bracket 86. A power supply 88 is coupled to video camera 84 through cable 90. Video camera 84 is mounted off the optical axis 34 and includes a lens 92 for viewing the patient's face (FIG. 7) during the ocular disease and abnormality detection procedure of the present invention. An elliptical mirror 94 is mounted to the video camera lens 92 to direct the video camera's field of view toward the patient's face (Fig, 7). To illuminate the patient's face for this purpose, a series of four infrared light emitting diodes (LED's) 96 are mounted on the lens 92 of video camera 84 and directed toward the patient's face. Infrared light emitted from the LED's 96 is not visible to the patient's eyes 16, but the video camera 84 is sensitive in the IR wavelength to provide images of the patient's face. A video display screen 98 is coupled to the video camera 84 through cable 100 for displaying real time images of the patient's face to the ophthalmologist or photoscreening technician. By viewing the patient's face in the video screen 98, the ophthalmologist or photoscreening technician can quickly check the patient's eyes 16 both for alignment and pupil dilation before a retinal reflection of the patient's eyes 16 is recorded by the photo-imaging device 24. Preferably, the brightness of the visual image 72 projected by the visual stimulus generator 70 is adjustable to permit pupil dilation of the patient's eyes to be adjusted. The ophthalmologist or photoscreening technician can readily increase or decrease the patient's pupil size by decreasing or increasing the brightness of visual image 72, respectively.

Figure 7:
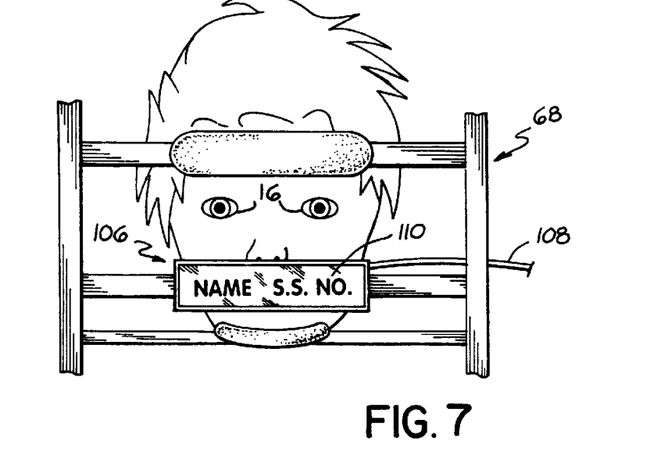
FIG. 7 is a schematic view showing a patient's head supported on a headrest of the ocular disease and abnormality detection device of the present invention.

Referring to FIGS. 1 and 7, it is preferred that the retinal reflection 26 from the patient's eyes 16 is stored and displayed with selected patient information, such as patient name and Social Security number. In one embodiment shown in FIG. 1, a keyboard 102 is coupled to computer 36 through cable 104 for entering text strings as a header file which is electronically stored with the recorded retinal reflections 26 from the patient's eyes 16. Alternatively, as shown in FIG. 7, a flat liquid crystal display (LCD) 106 may be coupled to the computer 36 through a cable 108. The LCD display 106 is mounted in front of the patient's face and below the patient's eyes 16 for electronically displaying selected patient information, shown diagrammatically as numeral 110. As the photo-imaging device 24 records the retinal reflection 26 from the patient's eyes 16, the patient information 110 displayed on the LCD display 106 will also be recorded with the retinal reflection. In either embodiment, as a particular patient's retinal reflection file is retrieved form computer storage and displayed on color video display 60, the selected patient information will also be displayed with the retinal reflection 26.

Figure 3:
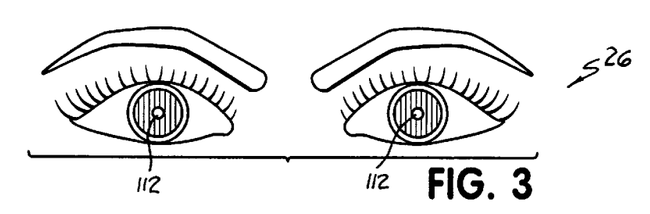
FIGS. 3–6 are illustrations of eyes of patients recorded by the ocular disease and abnormality detection device of the present invention.
Figure 4:
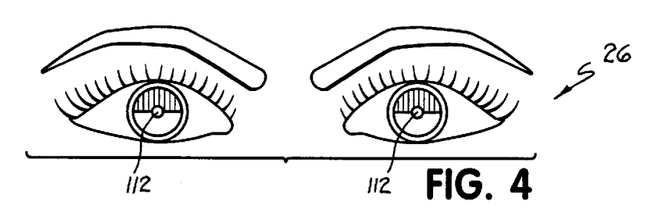
Figure 5:
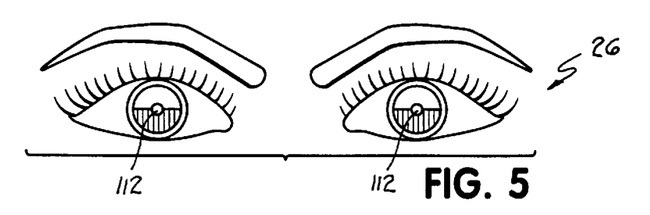
Figure 6:
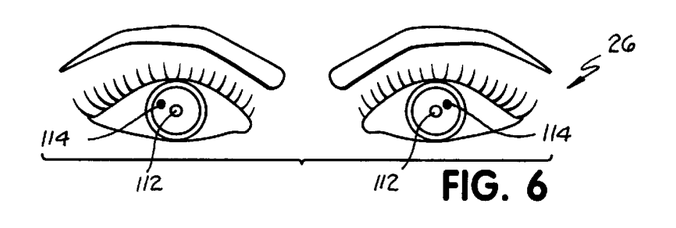

As shown in FIGS. 3–6, various retinal reflections 26 may be recorded by the photo-imaging device 10 and displayed in real-time or from computer storage on the color video display screen 60. As shown in FIG. 3, a clinically perfect eye produces a red retinal reflection 26 which is uniform across the pupil. The white spots 112 in the retinal reflection 26 are produced as points of light reflected from the cornea and are extremely useful in the diagnosis of strabismus. In clinically perfect human eyes, the white spots 112 are generally centered in the pupil. However, if a patient has a deviating optical axis, the white spot 112 reflected by the cornea will deviate from the center of the pupil which is readily visible from the displayed retinal reflection. FIG. 4 illustrates a retinal reflection 26 which identifies the refractive error of nearsightedness (myopia). In this case, the retinal reflection 26 is not uniformly red across the pupil, but rather has a red retinal reflection above the cornea and a white retinal reflection below the cornea. The severity of the nearsightedness (myopia) is indicated by the extent of nonuniformity in the retinal reflection. FIG. 5 illustrates a retinal reflection which identifies the refractive error of farsightedness (hypermetropia) wherein the red retinal reflection is generally reversed from retinal reflection produced by nearsightedness (myopia). FIG. 6 illustrates scarring of the cornea which is indicated by readily observable dark spots 114. By analyzing the visual characteristics of the retinal reflections 26 from the patient's eyes 16 as displayed on the color video display 60, the ophthalmologist is able to readily detect diseases and abnormalities in a patient's eyes 16.

During the ocular disease and abnormality detection procedure of the present invention, the patient's head is securely positioned in the adjustable headrest 68 (FIG. 7) to align the patient's eyes 16 on the optical axis 34. The patient's eyes 16 are spaced from the lens 28 of photo-imaging device 24 the predetermined focal distance "X" which preferably ranges from between about 30" to about 36". A flash beam of light is generated by flash device 46 and directed generally along the optical axis 34 with a slight angular separation to produce retinal reflections 26 (FIGS. 3–6) from the patient's eyes 16. The beamsplitter 64 passes the flash beam of light from the flash device 46 to the patient's eyes 16, and passes the retinal reflection 26 from the patient's eyes 16 to the lens 28 of the photo-imaging device 24. The visual image 72 is projected on the surface 74 of beamsplitter 64, and appears to the patient's eyes 16 as being positioned on the optical axis 34 and generally superimposed on the lens 28 of the photo-imaging device 24. The patient's eyes 16 generally focus on the lens 28 of the photo-imaging device 24 as the patient views the projected visual image 72, and the retinal reflection 26 from the patient's eyes is recorded by the photo-imaging device 24.

Figure 8:
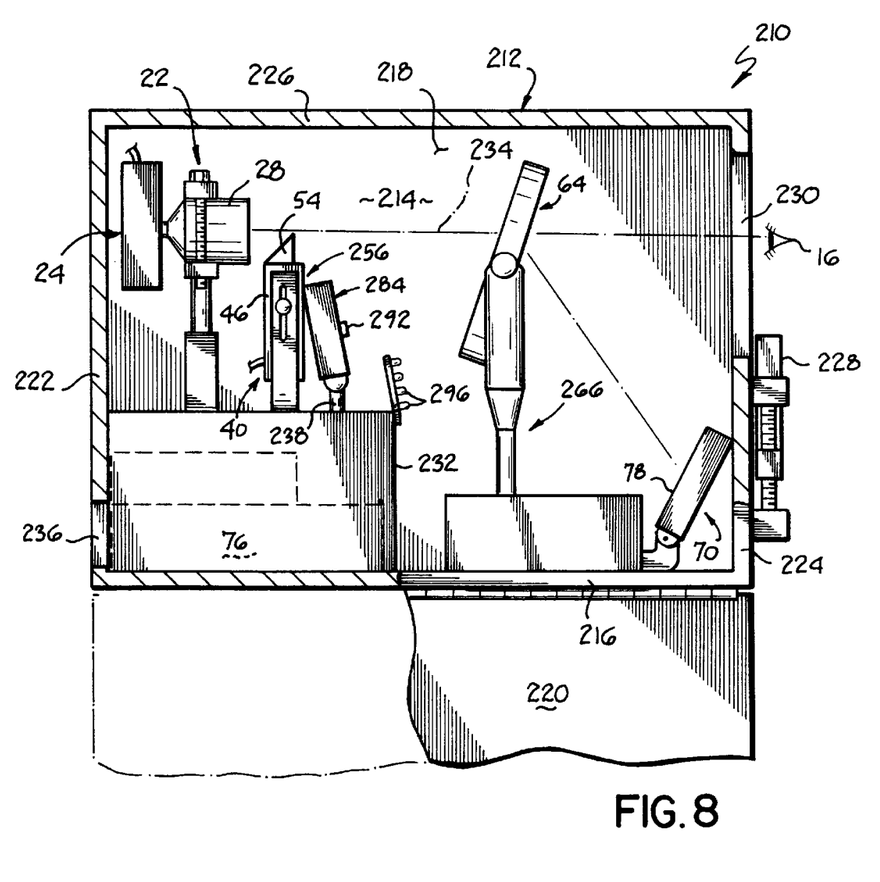
FIG. 8 is a side elevation view showing an alternative embodiment of the ocular disease and abnormality detection device of the present invention.

In an alternative embodiment of the present invention as shown in FIG. 8, a self-contained ocular disease and abnormality detection device 210 is shown including many of the same components as shown in the embodiment of FIGS. 1 and 2. For the sake of simplicity, like components in the various embodiments have been given like reference numerals, and should be assumed to operate in generally a like manner.

Ocular disease and abnormality detection device 210 preferably includes a housing 212 for enclosing various components of the detection device 210 in a compact chamber 214 which is portable between the various screening locations. The housing 212 is formed by a bottom wall 216, a fixed side wall 218, a hinged side wall 220, opposite end walls 222 and 224, and a top wall 226, each having a painted inner surface to substantially absorb light within the chamber 214.

As shown in FIG. 8, with hinged side wall 220 folded downwardly to an open position, photo-imaging device 24 is mounted at one end of the housing 212 remote from the patient's eyes 16. Photo-imaging device 24 is controlled by computer 36 (not shown) as described in detail above for receiving retinal reflections 26 (FIGS. 3–6) from the patient's eyes 16. Clamp assembly 22 is provided to securely hold the optical lens 28 in alignment with an optical axis 234 which is coincident with the position of the patient's eyes 16. An adjustable headrest (chin rest) 228 is mounted to an outer surface of end wall 224 for raising and lowering the patient's eyes 16 relative to the optical axis 234 and an aperture 230 formed in the end wall 224.

As described in detail above, flash unit 40 includes vertically adjustable flash device 46 and right angle prism 54 for generating a flash beam of light toward the patient's eyes 16. Vertical adjustment of flash device 46 and right angle prism 54 relative to the optical axis 234 is provided by an adjustable mount 256.

Substantially transparent pellicle beamsplitter 64 is pivotally supported on adjustable stand 266 within chamber 214. As described in detail above, beamsplitter 64 is positioned on the optical axis 234 intermediate the photo-imaging device 24 and adjustable headrest 228. Beamsplitter 64 is operable to pass the flash beam of light from flash device 46 to the patient's eyes 16, and to pass the retinal reflections 26 from the patient's eyes to the lens 28 of photo-imaging device 24 as set forth above.

Visual stimulus generator 70 is provided to assist in focusing the patient's eyes 16 on the lens 28 of photo-imaging device 24. A video cassette player 76 is coupled to flat video display screen 78 for projecting moving visual images 72 on the surface 74 of beamsplitter 64 (FIG. 2) that appear to the patient's eyes 16 as being superimposed on the lens 28 of photo-imaging device 24. Video cassette player 76 is housed within an enclosure 232 provided within chamber 214. An aperture 236 is preferably formed in the end wall 222 to provide access to user controls of the VCR 76. Preferably, one or more speakers (not shown) are connected to the video cassette player 76 and positioned near photo-imaging device 24 to further attract the child's eyes to the camera lens 28.

In accordance with the alternative embodiment of FIG. 8, a small greyscale video camera 284 is mounted on an upper surface of enclosure 232 through an adjustable support bracket 238. Video camera 284 is positioned off of the optical axis 234 and includes a lens 292 directed toward the patient's face (not shown) during the ocular disease and abnormality detection procedure. To illuminate the patient's face for this purpose, an array of light emitting diodes (L.E.D.'s) 296 are mounted below the field of view of video camera 284 and directed toward the patient's face. The video camera 284 is coupled to video display screen 98 (not shown) for displaying real-time images of the patient's face to the ophthalmologist or photoscreening technician. As described in detail above, video camera 284 allows the ophthalmologist or photoscreening technician to check the patient's eyes 16 both for alignment and pupil dilation before a retinal reflection is recorded.

Those skilled in the art will readily appreciate that ocular disease and abnormality detection devices 10 and 210 of the present invention advantageously assist in focusing the patient's eyes 16 on the lens 28 of photo-imaging device 24 during the ocular disease detection procedure. By superimposing the projected visual image 72 on the lens 28 of photo-imaging device 24, the patient generally focuses on the lens while viewing the projected image. Greyscale video camera 84 and video display screen 98 allow the ophthalmologist or photoscreening technician to readily check the patient's eyes for alignment and pupil dilation before a retinal reflection is recorded. Digital camera 24 and computer 36 provide the ability to display retinal reflections in real-time, or to retrieve and display stored retinal reflections at a future date. The ability to vary the brightness of the projected visual image 72 permits quick adjustment of pupil dilation in the patient's eyes before the ocular disease detection procedure is commenced.

From the above disclosure of the general principles of the present invention and the preceding detailed description of preferred embodiments, those skilled in the art will readily comprehend the various modifications to which the present invention is susceptible. The invention in its broader aspects is therefore not limited to the specific details and illustrative example shown and described. Accordingly, departures may be made from such details without departing from the spirit or scope of Applicants' general inventive concept.

Having described the invention, we claim:

1. Apparatus for detecting ocular disease and abnormalities, comprising:
   a headrest for supporting a patient's head and aligning the patient's eyes on a selected optical axis;
   a photo-imaging device having a lens aligned on said selected optical axis, said lens being spaced from said headrest a predetermined focal distance and operable to receive a retinal reflection from the patient's eyes;
   a flash unit for generating a flash beam of light generally along said selected optical axis and producing retinal reflections from the patient's eyes;
   a beamsplitter positioned on said selected optical axis, said beamsplitter being operable to pass the flash beam of light from the flash unit to the patient's eyes, and to pass the retinal reflections from the patient's eyes to the lens of said photo-imaging device; and
   a visual stimulus generator operable to project a visual image on a surface of said beamsplitter, said projected visual image appearing to the patient's eyes as being aligned on said selected optical axis and generally superimposed on the lens of said photo-imaging device at said predetermined focal distance whereby the patient's eyes generally focus on the lens of said photo-imaging device while viewing the projected visual image to permit accurate retinal reflections from the patient's eyes to be recorded by said photo-imaging device.

2. The apparatus of claim 1 wherein said photo-imaging device comprises a digital camera for electronically recording the retinal reflections from the patient's eyes.

3. The apparatus of claim 2 further comprising:
   a data processing unit coupled to said digital camera for receiving and storing the electronically recorded retinal reflections from the patient's eyes; and
   a video display screen coupled to said data processing unit for displaying the recorded retinal reflections of the patient's eyes.

4. The apparatus of claim 1 wherein said visual stimulus generator comprises;
   a video cassette player operable to generate a moving visual image; and
   a video display screen coupled to said video cassette player for projecting the moving visual image on the surface of said beamsplitter.

5. The apparatus of claim 1 wherein said visual stimulus generator is operable to vary the brightness of the projected visual image whereby pupil dilation of the patient's eyes may be adjusted by increasing or decreasing the brightness of the projected visual image.

6. The apparatus of claim 1 wherein said flash unit is adjustable relative to said selected optical axis to provide adjustable angular separation between the flash beam of light and said selected optical axis.

7. The apparatus of claim 6 wherein the angular separation between the flash beam of light and said selected optical axis is adjustable in a range from about 1° to about 5°.

8. The apparatus of claim 1 further comprising:
   an illumination source for illuminating the face of the patient while the patient's head is positioned in the headrest;
   a video camera positioned off the optical axis and operable to view the patient's face; and
   a video display screen coupled to the video camera for displaying a real-time image of the patient's face.

9. The apparatus of claim 8 wherein said illumination source comprises an infrared light source.

10. The apparatus of claim 1 further comprising a video display screen positioned adjacent the headrest for displaying selected patient information whereby the patient information is recorded by said photo-imaging device with retinal reflections from the patient's eyes.

11. The apparatus of claim 3 further comprising a data entry device coupled to said data processing unit for entering selected patient information whereby the patient information is stored and displayed with the recorded retinal reflections of the patient's eyes.

12. Apparatus for detecting ocular disease and abnormalities, comprising:
   a headrest for supporting a patient's head and aligning the patient's eyes on a selected optical axis;
   a photo-imaging device having a lens aligned on said selected optical axis, said lens being spaced from said headrest a predetermined focal distance and facing toward said headrest for receiving a retinal reflection from the patient's eyes;
   a flash device positioned off the optical axis for generating a flash beam of light in a direction generally perpendicular to the optical axis;
   a prism associated with said flash device for aligning the flash beam of light generally along said selected optical axis whereby the flash beam of light produces retinal reflections from the patient's eyes;
   a beamsplitter positioned on said selected optical axis intermediate said photo-imaging device and said headrest, said beamsplitter being operable to pass the flash beam of light from the flash device to the patient's eyes, and to pass the retinal reflections from the patient's eyes to the lens of said photo-imaging device; and
   a visual stimulus generator positioned off said selected optical axis and operable to project a visual image on a surface of said beamsplitter, said projected visual image appearing to the patient's eyes as being aligned on said selected optical axis and generally superimposed on the lens of said photo-imaging device at said predetermined focal distance whereby the patient's eyes generally focus on the lens of said photo-imaging device while viewing the projected visual image to permit accurate retinal reflections from the patient's eyes to be recorded by said photo-imaging device.

13. The apparatus of claim 12 wherein said photo-imaging device comprises a digital camera for electronically recording the retinal reflections from the patient's eyes.

14. The apparatus of claim 13 further comprising:
a data processing unit coupled to said digital camera for receiving and storing the electronically recorded retinal reflections from the patient's eyes; and
a video display screen coupled to said data processing unit for displaying the recorded retinal reflections of the patient's eyes.

15. The apparatus of claim 12 wherein said visual stimulus generator comprises;
a video cassette player operable to generate a moving visual image; and
a video display screen coupled to said video cassette player for projecting the moving visual image on the surface of said beamsplitter.

16. The apparatus of claim 12 further comprising:
an illumination source for illuminating the face of the patient while the patient's head is positioned in the headrest;
a video camera positioned off said selected optical axis and operable to view the patient's face; and
a video display screen coupled to the video camera for displaying a real-time image of the patient's face.

17. Apparatus for detecting ocular disease and abnormalities, comprising:
a headrest for supporting a patient's head and aligning the patient's eyes on a selected optical axis;
a digital camera having a lens aligned on said selected optical axis, said lens being spaced from said headrest a predetermined focal distance and operable to receive a retinal reflection from the patient's eyes;
a flash unit for generating a flash beam of light generally along said selected optical axis and producing retinal reflections from the patient's eyes which are electronically recorded by the digital camera;
an illumination source for illuminating the face of the patient while the patient's head is positioned in the headrest;
a video camera operable to view the patient's face;
a video display screen coupled to the video camera for displaying a real-time image of the patient's face;
a beamsplitter positioned on said selected optical axis, said beamsplitter being operable to pass the flash beam of light from the flash unit to the patient's eyes, and to pass the retinal reflections from the patient's eyes to the lens of said digital camera; and
a visual stimulus generator operable to project a visual image on a surface of said beamsplitter, said projected visual image appearing to the patient's eyes as being aligned on said selected optical axis and generally superimposed on the lens of said digital camera at said predetermined focal distance whereby the patient's eyes generally focus on the lens of said digital camera while viewing the projected visual image to permit accurate retinal reflections from the patient's eyes to be recorded by said digital camera.

18. The apparatus of claim 17 further comprising:
a data processing unit coupled to said digital camera for receiving and storing the electronically recorded retinal reflections from the patient's eyes; and
a video display screen coupled to said data processing unit for displaying the recorded retinal reflections of the patient's eyes.

19. The apparatus of claim 17 wherein said visual stimulus generator comprises;
a video cassette player operable to generate a moving visual image; and
a video display screen coupled to said video cassette player for projecting the moving visual image on the surface of said beamsplitter.

20. The apparatus of claim 19 wherein said illumination source comprises an infrared light source.

21. A method of detecting ocular disease and abnormalities, comprising:
aligning eyes of a patient on a selected optical axis;
aligning a lens of a photo-imaging device on said selected optical axis;
spacing the lens of the photo-imaging device from the patient's eyes a predetermined focal distance;
directing a flash beam of light generally along said selected optical axis to produce retinal reflections from the patient's eyes;
providing a beamsplitter on said selected optical axis, the beamsplitter being operable to pass the flash beam of light to the patient's eyes, and to pass the retinal reflections from the patient's eyes to the lens of the photo-imaging device;
projecting a visual image on the beamsplitter whereby the projected visual image appears to the patient's eyes as being aligned on said selected optical axis and generally superimposed on the lens of the photo-imaging device at said predetermined focal distance, and whereby the patient's eyes generally focus on the lens of the photo-imaging device while viewing the projected visual image; and
recording retinal reflections from the patient's eyes with the photo-imaging device.

22. The method of claim 21 further comprising displaying the recorded retinal reflections from the patient's eyes on a video display screen.

23. The method of claim 21 further comprising:
illuminating the patient's face while the eyes of the patient are aligned on said selected optical axis;
viewing the patient's face; and
displaying a real-time image of the patient's face on a video display screen.

24. The method of claim 21 further comprising linking selected patient information with the recorded retinal reflections from the patient's eyes.

25. A method of detecting ocular disease and abnormalities, comprising:
aligning eyes of a patient on a selected optical axis;
aligning a lens of a digital camera on said selected optical axis;
spacing the lens of the digital camera from the patient's eyes a predetermined focal distance;
directing a flash beam of light generally along said selected optical axis to produce retinal reflections from the patient's eyes;
providing a beamsplitter on said selected optical axis, the beamsplitter being operable to pass the flash beam of light to the patient's eyes, and to pass the reflections from the patient's eyes to the lens of the digital camera;
projecting a visual image on the beamsplitter whereby the projected visual image appears to the patient's eyes as being aligned on said selected optical axis and generally superimposed on the lens of the digital camera at said predetermined focal distance, and whereby the patient's eyes generally focus on the lens of the digital camera while viewing the projected visual image; and electronically recording retinal reflections from the patient's eyes with the digital camera.

26. Apparatus for detecting ocular disease and abnormalities, comprising:

a headrest for supporting a patient's head and aligning the patient's eyes on a selected optical axis;

a photo-imaging device having a lens aligned on said selected optical axis, said lens being spaced from said headrest a predetermined focal distance and operable to receive a retinal reflection from the patient's eyes;

a flash unit for generating a flash beam of light generally along said selected optical axis and producing retinal reflections from the patient's eyes;

a beamsplitter positioned on said selected optical axis, said beamsplitter being operable to pass the retinal reflections from the patient's eyes to the lens of said photo-imaging device; and a visual stimulus generator operable to project a visual image on a surface of said beamsplitter, said projected visual image appearing to the patient's eyes as being aligned on said selected optical axis and generally superimposed on the lens of said photo-imaging device at said predetermined focal distance whereby the patient's eyes generally focus on the lens of said photo-imaging device while viewing the projected visual image to permit accurate retinal reflections from the patient's eyes to be recorded by said photo-imaging device.

* * * * *